United States Patent [19]

Kurkov

[11] 4,031,115

[45] June 21, 1977

[54] 4-PENTENOIC ACID CONVERSION

[75] Inventor: Victor P. Kurkov, San Rafael, Calif.

[73] Assignee: Chevron Research Company, San Francisco, Calif.

[22] Filed: Mar. 29, 1976

[21] Appl. No.: 671,880

[52] U.S. Cl. ............................................. 260/343.6
[51] Int. Cl.$^2$ ....................................... C07D 307/32
[58] Field of Search ................................. 260/343.6

[56] References Cited

OTHER PUBLICATIONS

Arnold, et al., JACS 75:1044–1047 (3–53).
van Tamelen, et al., JACS 76:2315–2317 (5–54).
de Moura Campos, et al., Chem. Abs. 63:4159–4160 (1965).
Bresson, et al., Chem. Abs. 75:20067d (1971).

*Primary Examiner*—Cecilia M. S. Jaisle
*Attorney, Agent, or Firm*—Dix A. Newell; John Stoner, Jr.; W. Keith Turner

[57] ABSTRACT

A method for preparing a gamma-chloromethyl-gamma-butyrolactone which comprises contacting 4-pentenoic acid with air or oxygen and a catalyst comprising a noble metal halide, a variable valence transition metal halide and an alkali metal halide at a temperature between 50° and 200° C and superatmospheric pressure.

7 Claims, No Drawings

4-PENTENOIC ACID CONVERSION

BACKGROUND OF THE INVENTION

The present invention is directed to the preparation of a gamma-chloromethyl-gamma-butyrolactone which is useful as a solvent, for example, for acetylene, epoxy resins, and polyvinyl chloride copolymers and other resins. Previous methods of making lactones in general have been by conversion of gamma-hydroxy acids to gamma-lactones as follows:

$$R-CH(OH)-CH_2-CH_2-CO_2H \xrightarrow{heat} \begin{array}{c} R-CH-CH_2 \\ | \quad \quad | \\ O \quad CH_2 \\ \diagdown C \diagup \\ \| \\ O \end{array} + HOH$$

See, for example, Cason, *Principles of Modern Organic Chemistry*, Prentice-Hall, Inc., 1966. Morrison and Boyd, *Organic Chemistry*, 2nd Ed., Allyn and Bacon, Inc., Boston, 1970, give the reaction as follows for the salt of a gamma-hydroxy acid:

$$RCHCH_2CH_2COO^-Na^+ \underset{OH^-}{\overset{H^+}{\rightleftarrows}} \begin{array}{c} O \\ \| \\ C \\ H_2C \diagdown \quad \diagdown \\ | \quad \quad O \\ H_2C \diagup \\ CHR \end{array}$$

Commercially gamma-butyrolactone is made from 1,4-butanediol by oxidative cyclization. However, the diol is believed to first be converted to the hydroxy acid before the cyclization occurs so that the cyclization would be as given in the above equations.

A synthesis of the analogous iodolactone was reported by E. E. Van Tamelen et al, *J. Am. Chem. Soc.*, 76, 2315 (1953). The lactone was made from 4-pentenoic acid and a stoichiometric amount of iodine.

SUMMARY OF THE INVENTION

According to the present invention a method is provided for preparing a gamma-chloromethyl-gamma-butyrolactone which comprises contacting 4-pentenoic acid with oxygen and a catalyst comprising a noble metal halide, a variable valence transition metal halide and an alkali metal halide at a temperature between 50° and 200° C and superatmospheric pressure. The oxygen may be supplied for the reaction in the form of air.

Preferred operating conditions for the method of the present invention are as follows:

|  | Preferred | More Preferred | Most Preferred |
|---|---|---|---|
| Temperature, ° C | 50–200 | 60–150 | 75–125 |
| Pressure, atm. | 1–40 | 5–30 | 7–20 |
| Feed | — | — | 4-pentenoic acid |
| Solvent | polar inert solvents | nitriles 3°-amides sulfoxides | benzonitrile |
| Catalyst (e.g. Pd or Pt/Cu/Li) | | | |
| PdCl$_2$, PtCl$_2$, mol % | .01–10 | 0.5–5 | 1–5 |
| CuCl$_2$ | .1–40 | 3–30 | 5–25 |
| LiCl | .1–50 | 5–40 | 10–30 |

The term "noble metal catalyst" is used herein to mean ruthenium, rhodium, palladium, osmium, iridium and platinum. Palladium and platinum are particularly preferred noble metal catalysts for the present preparation method.

The term "variable valence transition metals" is used herein to mean those transition elements which can change their valence state by oxidation reduction. More specifically, transition metals which can be oxidized to their higher oxidation state by air or oxygen. Preferred transition metal catalysts are copper and iron. Particularly preferred as to the transition metal catalysts is copper.

The term "alkali metal" is used herein to mean Group IA metals. Of these metals lithium, sodium, and potassium are preferred and lithium is especially preferred.

The reaction equation for the method of the present invention may be given as follows:

$$H_2C=CH-CH_2-CH_2-C\begin{array}{c}\diagup O \\ \diagdown OH\end{array} + HCl + \tfrac{1}{2}O_2 \rightarrow \begin{array}{c} CH_2-CH_2 \\ | \quad \quad | \\ CH \quad C=O \\ \diagup \quad \diagdown \quad \diagup \\ CH_2Cl \quad O \end{array} + H_2O$$

EXAMPLES

A glass pressure reactor was charged with:

| A glass pressure reactor was charged with: | |
|---|---|
| benzonitrile | 25 ml |
| 4-pentenoic acid | 5.0 g (50 mmols) |
| CuCl$_2$ | 4.1 g (30.5 mmols) |
| LiCl | 0.65 g (15.3 mmols) |
| PdCl$_2$ | 0.81 g (4.6 mmols) |
| Toluene | 1.50 g |

The reactor was provided with a magnetic stirrer and was connected to an oxygen reservoir through a pressure regulator. The reactor was heated to 100° C and the pressure adjusted to 100 psig. The reaction was continued at constant pressure for 1 hour. The reactor was cooled, depressurized and the products analyzed by gas chromatography. The analysis showed 100% conversion of 4-pentenoic acid and a 67% yield of product gamma-chloromethyl-gamma-butyrolactone.

The following analyses identified the product as gamma-chloromethyl-gamma-butyrolactone:

Infrared (IR) peaks at
1770 cm$^{-1}$, C=O bond
1180 cm$^{-1}$, C—O bond
743 cm$^{-1}$, C—Cl bond
Nuclear Magnetic Resonance (NMR)
proton signals at 2.53 ppm, (m), 4H
proton signals at 3.76 ppm, (d), 2H
proton signals at 4.80 ppm, (m), 1H
Mass Spectroscopy (MS)
Molecular weight = 134
Elemental Analysis by weight

|  | Found | Calculated for $C_5H_7O_2Cl$ |
|---|---|---|
| %C | 44.91 | 44.6 |
| %H | 5.15 | 5.2 |
| %Cl | 27.20 | 26.3 |

Table I below shows several further runs carried out under the conditions as summarized in the table.

TABLE I

| Catalyst (mmols) | | | Solvent | Time, Hrs. | Conv. | Yield* mol% | Run No. |
|---|---|---|---|---|---|---|---|
| $PtCl_2$ (4.6) | $CuCl_2$ (30.5) | LiCl (15.3) | Benzonitrile | 1 | 95.2 | 82.8 | -05 |
| $PtCl_2$ (2.3) | $CuCl_2$ (30.5) | LiCl (15) | Benzonitrile | 1 | 92.6 | 90.7 | -07 |
| $PtCl_2$ (4.7) | $CuCl_2$ (30.5) | LiOAc (15) | HOAc | 1 | 87.0 | 82.9 | -06 |
| $PtCl_2$ (2.3) | $Cu(OAc)_2$ (30) | LiOAc (15) | HOAc | 1 | 24.9 | — | -17 |
| $PdCl_2$ (4.7) | $CuCl_2$ (30.5) | LiCl (15) | HOAc | 1 | 100 | 30.2 | -03 |

*gamma-chloromethyl-gamma-butyrolactone
Charge: Solvent — 25 ml
4-pentenoic acid — 46 mmol
toluene
Catalyst: as shown in millimols (mmols)
Oxygen Pressure: 100 psig As shown in the table, a surprisingly high yield of 90.7 mol percent of the desired product was obtained in run number −07 using the platinum catalyst and wherein the transition metal component of the catalyst was a halide. In run member −17, which also used a platinum catalyst, copper acetate was used instead of copper chloride, and an essentially nil yield of product gamma-chloromethyl-gamma-butyrolactone was obtained.

I claim:

1. A method for preparing a gamma-chloromethyl-gamma-butyrolactone which comprises contacting 4-pentenoic acid with oxygen and a catalyst comprising a noble metal chloride, a copper or iron chloride and an alkali metal chloride at a temperature between 50° and 200° C and superatmospheric pressure.

2. A process in accordance with claim 1 wherein the temperature is 75° to 125° C.

3. A process in accordance with claim 2 wherein the halide is chloride and wherein the noble metal is platinum or palladium, the transition metal is copper, and the alkali metal is lithium.

4. A process in accordance with claim 3 wherein the reaction is carried out in the presence of a nitrile solvent.

5. A process in accordance with claim 4 wherein the solvent is benzonitrile.

6. A process in accordance with claim 3 wherein the catalyst comprises 0.01 to 10 parts platinum or palladium chloride, 0.1 to 40 parts cuprous chloride, and 0.1 to 50 parts lithium chloride wherein the parts are on a molar basis.

7. A process for preparing a gamma-chloromethyl-gamma-butyrolactone which comprises contacting 4-pentenoic acid, oxygen and hydrochloric acid in the presence of a catalyst comprising a noble metal chloride, a copper or iron chloride, and an alkali metal chloride at a temperature between 50° and 200° C and superatmospheric pressure.

* * * * *